United States Patent [19]

Hesse et al.

[11] Patent Number: 4,929,733

[45] Date of Patent: May 29, 1990

[54] PREPARATION OF N-HETEROCYCLES

[75] Inventors: Michael Hesse, Ludwigshafen; Wolfgang Hoelderich, Frankenthal; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 207,861

[22] Filed: Jun. 17, 1988

[30] Foreign Application Priority Data

Jul. 1, 1987 [DE] Fed. Rep. of Germany ....... 3721777

[51] Int. Cl.$^5$ ................... C07D 207/06; C07D 211/14
[52] U.S. Cl. .................................... 546/184; 548/400; 546/348
[58] Field of Search ............... 546/184, 192, 195, 205, 546/203, 348; 548/577, 579, 400

[56] References Cited

U.S. PATENT DOCUMENTS

| | | | |
|---|---|---|---|
| 3,334,103 | 8/1967 | Feldman et al. | 260/290 |
| 3,502,692 | 3/1970 | Feldman et al. | 260/326.3 |
| 4,166,814 | 9/1979 | Karrer | 260/45.75 N |

FOREIGN PATENT DOCUMENTS 0101921  4/1986  European Pat. Off.
 857426 12/1960  United Kingdom .

OTHER PUBLICATIONS

Robertson et al., Hypotensives V 2,2,6,6-Tetramethyl-piperidines and Related Compounds, J. Med. Chem. 6(1963), 4, pp. 381-384.
C. A., vol. 95, 219971.

Primary Examiner—Mary C. Lee
Assistant Examiner—Jacqueline Haley
Attorney, Agent, or Firm—Keil & Weinkauf

[57] ABSTRACT

N-heterocycles of the general formulae (I) and (II)

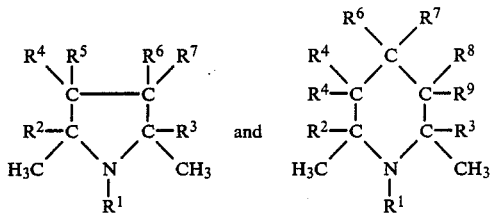

where $R^1$ and $R^4$ to $R^9$ are each hydrogen, alkyl, aryl, aralkyl, alkylaryl or cycloalkyl and $R^2$ and $R^3$ are each an alkyl, alkylaryl, substituted alkyl or cycloalkyl group, are prepared by a process in which an olefin of the formula (III) or (IV)

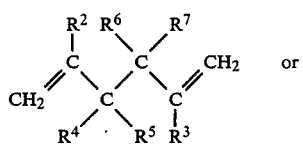

or

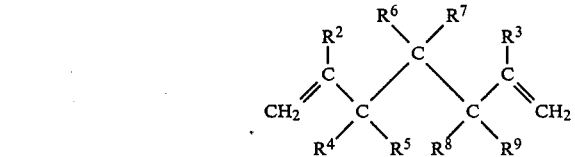

where $R^2$ to $R^9$ have the above meanings, is reacted with $NH_3$ or with a primary amine of the formula $H_2NR^1$, where $R^1$ has the above meanings, in the presence of a zeolite as a catalyst.

9 Claims, No Drawings

PREPARATION OF N-HETEROCYCLES

The present invention relates to a process for the preparation of N-heterocycles by reacting olefins of the formulae (III) and (IV) with NH₃ or primary amines in the presence of zeolites as catalysts.

Saturated N-heterocycles, such as pyrrolidines or piperidines, are desirable starting materials in the chemistry of active substances and can be prepared by several methods (Bird and Cheeseman: Comprehensive Heterocyclic Chemistry 4, pages 89–154 and Boulton and McKillop: Comprehensive Heterocyclic Chemistry 2, pages 67–98). However, the preparation of compounds of the abovementioned class, in which the nitrogen atom is shielded by bulky α-groups, eg. 2,2,6,6-tetramethylpiperidine, presents difficulties. These substances are obtainable in a few specific cases by reacting condensates of acetone, eg. phorone, with ammonia (German Patents 2,412,750 and 2,352,127). In the procedure, NH₃ is subjected to an addition reaction with α,β-unsaturated carbonyl compounds with cyclization. The carbonyl function must then be hydrogenated separately in order to obtain the desired products. This involves a multi-stage process. In contrast, it is not possible to react nonactivated olefins by this method.

It is known that amines can be reacted with olefins, preferably with olefins substituted at the double bond, over acidic ion exchangers (U.S. Pat. No. 4,536,602) and over zeolites to give substituted amines (German Patents 3,326,579 and 3,327,000, U.S. Pat. No. 4,375,002 and European Patents 39,918, 77,016 and 101,921).

However, only the addition reaction of NH₃ with monoolefins or only the addition of NH₃ at a double bond of a polyunsaturated compound is described here. The formation of cyclic amines by intramolecular reaction of two double bonds is not disclosed.

It is an object of the present invention to provide a process which permits the selective preparation of 5-membered and 6-membered N-heterocycles which are substituted by sterically bulky groups, as described in formulae (I) and (II), without the necessity of a multi-stage reaction.

We have found that this object is achieved in that, surprisingly, in the reaction of nonconjugated diolefins with ammonia or primary amines in the presence of zeolites as catalysts, saturated N-heterocycles are obtained, formed by addition of the amine across both double bonds with cyclization.

The present invention relates to a process for the preparation of N-heterocycles of the general formulae (I) and (II)

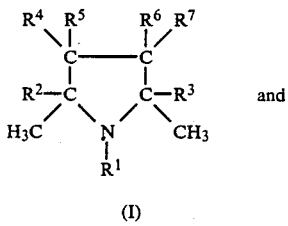 and 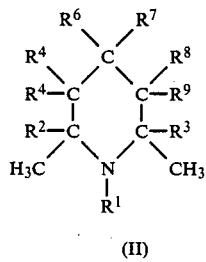

(I) (II)

where $R^1$ and $R^4$ to $R^9$ are each hydrogen, alkyl, aryl, aralkyl, alkylaryl or cycloalkyl and $R^2$ and $R^3$ are each an alkyl, alkylaryl, substituted alkyl or cycloalkyl group, wherein an olefin of the formula (III) or (IV)

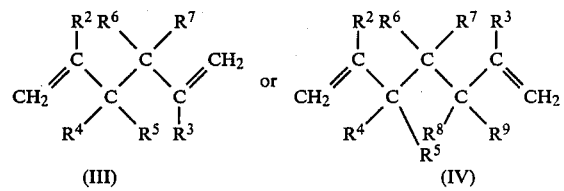

(III) (IV)

where $R^2$ and $R^9$ have the above meanings, is reacted with NH₃ or with a primary amine of the formula H₂NR¹, where $R^1$ has the above meanings, in the presence of a zeolite as a catalyst.

Olefins of the formulae (III) and (IV) which, according to the invention, may be preferably reacted as starting materials are, for example, 2,5-dimethyl-1,5-hexadiene and 2,6-dimethyl-1,6-dimethylheptadiene.

Examples of the amines reacted according to the invention are ammonia, methylamine, ethylamine, cyclopentylamine, cyclohexylamine, aniline and toluidines.

The catalysts used for the novel process are zeolites, in particular those of the pentasil type. The zeolites are advantageously used in the acidic form. Zeolites are crystalline aluminum silicates which have a highly ordered structure with a rigid three-dimensional network of SiO₄ and AlO₄ tetrahedra which are bonded by common oxygen atoms. The ratio of Si and Al atoms to oxygen is 1:2. The electrovalency of the aluminum containing tetrahedra is compensated by the inclusion of cations in the crystal, for example an alkali metal or hydrogen ion. Cation exchange is possible. Voids between the tetrahedra are occupied by water molecules prior to dehydration by drying or calcination.

In the zeolites, other elements, such as B, Ga, Fe, Cr, V, As, Sb, Bi or Be or a mixture of these, may be incorporated in the framework instead of aluminum, or the silicon may be replaced by a tetravalent element, such as Ge, Ti, Zr or Hf.

Zeolites are divided into various groups, according to their structure. For example, the zeolite structure is formed by chains of tetrahedra in the mordenite group and by sheets of tetrahedra in the chabasite group, whereas in the faujasite group the tetrahedra are arranged to form polyhedra, for example in the form of a cubooctahedron, which is composed of 4-membered rings and 6-membered rings. Depending on the bonding of the cubooctahedra, which gives rise to cavities and pores of different sizes, a distinction is made among zeolites of type A, L, X and Y.

Suitable catalysts for the novel process are, for example, zeolites of the mordenite group or finepore zeolites of the erionite or chabasite type or zeolites of the faujasite type, for example Y, X or L zeolites.

This group of zeolites also includes the ultrastable zeolites of the faujasite type, ie. dealuminated zeolites. Processes for the preparation of such zeolites have been described in many publications.

Zeolites of the pentasil type are particularly advantageous. They have, as a common building block, a 5-membered ring composed of SiO₄ tetrahedra. They possess a high SiO₂/Al₂O₃ ratio and pore sizes which are between those of the zeolites of type A and those of type X or Y.

These zeolites may have different chemical compositions. They are aluminosilicate, borosilicate, iron silicate, beryllium silicate, gallium silicate, chromium silicate, arsenosilicate, antimony silicate and bismuth silicate zeolites or mixtures of these, as well as aluminogermanate, borogermanate, gallium germanate and iron germanate zeolites or mixtures of these. The aluminosilicate, borosilicate and iron silicate zeolites of the pentasil type are particularly suitable for the novel process. The aluminosilicate zeolite is prepared, for example, from an aluminum compound, preferably $Al(OH)_3$ or $Al_2(SO_4)_3$, and a silicon component, preferably finely divided silica, in aqueous amine solution, in particular in a polyamine, such as 1,6-hexanediamine or 1,3-propanediamine or triethylenetetramine solution, with or, in particular, without the addition of an alkali or alkaline earth, at from 100 to 220° C. under autogenous pressure. They also include the isotactic zeolites according to European Patents 34,727 and 46,504. The aluminosilicate zeolites obtained have an $SiO_2/Al_2O_3$ ratio of from 10 to 40,000, depending on the amounts of starting materials chosen. Aluminosilicate zeolites of the pentasil type can also be synthesized in an ether medium, such as diethylene glycol dimethyl ether, in an alcohol medium, such as methanol or 1,4-butanediol, or in water.

The silicon-rich zeolites ($SiO_2/Al_2O_3 \geq 10$) which can be used according to the invention include the various ZSM types, ferrierite, Nu-1 and Silicalit ®.

Borosilicate zeolites can be synthesized, for example, at from 90 to 200° C. under autogenous pressure by reacting a boron compound, eg. $H_3BO_3$, with a silicon compound, preferably finely divided silica, in aqueous amine solution, in particular in 1,6-hexanediamine or 1,3-propanediamine or triethylenetetramine solution, with or, in particular, without the addition of an alkali or alkaline earth. These also include the isotactic zeolites according to European Patents 34,727 and 46,504. Such borosilicate zeolites can also be prepared if the reaction is carried out in ether solution, for example diethylene glycol dimethyl ether, or in alcoholic solution, for example hexane-1,6-diol, instead of in aqueous amine solution.

The iron silicate zeolite is obtained, for example, from an iron compound, preferably $Fe_2(SO_4)_3$, and a silicon compound, preferably finely divided silica, in aqueous amine solution, in particular 1,6-hexanediamine, with or without the addition of an alkali or alkaline earth at from 100 to 200° C. under autogenous pressure.

The aluminosilicate, borosilicate and iron silicate zeolites thus prepared can be isolated, dried at from 100 to 160° C., preferably 110° C., calcined at from 450 to 550° C., preferably 500° C., and then molded with a binder in a weight ratio of from 90:10 to 40:60 to give extrudates or pellets. Suitable binders are various aluminas, preferably boehmite, amorphous aluminosilicates having an $SiO_2/Al_2O_3$ ratio of from 25:75 to 90:5, preferably 75:25, silica, preferably finely divided $SiO_2$, mixtures of finely divided $SiO_2$ and finely divided $Al_2O_3$, $TiO_2$, $ZrO_2$ and clay. After the molding procedure, the extrudates or pellets are dried at 110° C. for 16 hours and calcined at 500° C. for 16 hours.

Very effective catalysts are also obtained if the aluminosilicate or borosilicate zeolite isolated is molded directly after drying and is subjected to calcination only after the molding procedure. The aluminosilicate and borosilicate zeolites prepared can be used in pure form, without a binder, as extrudates or pellets, examples of extrusion or peptizing assistants used being ethylcellulose, stearic acid, potato starch, formic acid, oxalic acid, acetic acid, nitric acid, ammonia, amines, silicoesters and graphite as well as mixtures of these. If, because of its method of preparation, the zeolite is not in the catalytically active, acidic H form but, for example, in the Na form, the latter can be completely or partially converted into the desired H form by ion exchange, for example by ammonium ions, followed by calcination, or by treatment with acids.

In order to achieve very high selectivity, high conversion and a long catalyst life, it is advantageous to modify the zeolites. In a suitable method for modifying the catalysts, for example, the unmolded or molded zeolites are doped with metal salts by ion exchange or by impregnation. The metals used are alkali metals, such as Li, Cs or K, alkaline earth metals, such as Mg, Ca, Sr or Ba, metals of main groups 3, 4 and 5, such as B, Al, Ga, Ge, Sn, Pb or Bi, rare earth metals, such as La, Ce, Pr, Nd, Er, Yb and U, and noble metals. Modification with these metals may also be effected by ion exchange or impregnation.

In another possible method of modification, the molded or unmolded zeolite material is subjected to a treatment with acids, such as hydrochloric acid, hydrofluoric acid and phosphoric acid, and/or steam.

This doping is advantageously carried out as follows: the molded zeolite is initially taken in a riser tube, and an aqueous or ammoniacal solution of a halide or of a nitrate of the metals described above is passed over the said zeolite at from 20 to 100° C. Ion exchange of this type can be carried out on the hydrogen, ammonium and alkali metal form of the zeolite. In another possible method for applying the metals to the zeolite, the zeolite material is impregnated, for example, with a halide, a nitrate or an oxide of the metals described above, in aqueous, alcoholic or ammoniacal solution. Both ion exchange and impregnation are followed by one or more drying steps and, if desired, repeated calcination.

In a possible embodiment, for example, $Cu(NO_3)_2 \cdot 3H_2O$ or $Ni(NO_3)_2 \cdot 6H_2O$ or $Ce(NO_3)_3 \cdot 6H_2O$ or $Cr(NO_3)_3 \cdot 6H_2O$ or $Pd(NO_3)_2$ is dissolved in water and this solution is used to impregnate the molded or unmolded zeolite for a certain time, for example 30 minutes. Any supernatant solution is freed from water in a rotary evaporator. Thereafter, the impregnated zeolite is dried at about 150° C. and calcined at about 500° C. This impregnation process may be carried out several times in succession in order to obtain the desired metal content.

It is also possible to prepare an aqueous $Ni(NO_3)_2$ solution or ammoniacal $Pd(NO_3)_2$ solution and to suspend the pure zeolite powder therein at from 40 to 100° C. for about 24 hours, while stirring. After the product has been filtered off, dried at about 150° C. and calcined at about 500° C., the zeolite material thus obtained can be further processed with or without a binder to give extrudates, pellets or fluidizable material.

The zeolite in the H form or ammonium form or alkali metal form can be subjected to ion exchange by initially taking the zeolite, in the form of extrudates or pellets, in a column, and circulating, for example, an aqueous $Ni(NO_3)_2$ solution of ammoniacal $Pd(NO_3)_2$ solution over the said zeolite at slightly elevated temperatures of from 30 to 80° C. for from 15 to 20 hours. Thereafter, the product is washed thoroughly with water, dried at about 150° C. and calcined at about 550° C.

In the case of some metal-doped zeolites, for example Pd-, Cu- and Ni-doped zeolites, an aftertreatment with hydrogen is advantageous.

Specifically, in an advantageous procedure, the zeolites in powder form are treated with 1 N phosphoric acid for 1 hour at 80° C. After the treatment, the product is washed with water, dried at 110° C. for 16 hours and calcined at 500° C. for 20 hours. In another procedure, the zeolites before or after they have been molded with a binder, are treated with a 3-25, in particular 12-20, % strength by weight aqueous hydrochloric acid, for example for from 1 to 3 hours at from 60 to 80° C. The zeolite treated in this manner is then washed with water, dried, and calcined at from 400 to 500° C.

In a particular embodiment of the acid treatment, the zeolite material, before it has been molded, is treated at elevated temperatures with hydrofluoric acid, which in general is used in the form of 0.001-2 N, preferably 0.05-0.5 N, hydrofluoric acid, for example by refluxing for from 0.5 to 5, preferably from 1 to 3, hours. After the zeolite material has been isolated, for example by filtering it off and washing it thoroughly, it is advantageously dried at from 100 to 160° C. and calcined at from 450 to 600° C. In another preferred embodiment of the acid treatment, the zeolite material, after it has been molded with a binder, is treated at elevated temperatures, advantageously at from 50 to 90° C., preferably from 60 to 80° C., for from 0.5 to 5 hours, preferably with 12-20% strength by weight hydrochloric acid. The zeolite material is advantageously then washed thoroughly, dried at from 100 to 160° C. and calcined at from 450 to 600° C. An HF treatment may also be followed by an HCl treatment.

In another procedure, zeolites may be modified by applying phosphorus compounds, such as trimethoxy phosphate, trimethoxyphosphine or primary, secondary or tertiary sodium phosphate. The treatment with primary sodium phosphate has proven particularly advantageous. In this procedure, the zeolites in the form of extrudates, pellets or fluidizable material, are impregnated with aqueous $NaH_2PO_4$ solution, dried at 110° C. and calcined at 500° C.

If, when the zeolite catalysts are used according to the invention, deactivation due to coking occurs, it is advisable to regenerate the said catalysts by burning off the coke deposit with air or with an air/$N_2$ mixture at from 400 to 550° C., preferably 500° C. As a result, the zeolites regain their initial activity.

By precoking, it is possible to adjust the activity of the catalyst to achieve optimum selectivity with respect to the desired reaction product.

The catalysts described here can alternatively be used in the form of 2-4 mm extrudates, pellets of 3-5 mm diameter or chips having particle sizes of from 0.1 to 0.5 mm or in the form of a fluidized catalyst.

The reaction conditions generally chosen for the novel reaction are from 50 to 500° C., eg. from 150 to 450° C., in particular from 200 to 400° C., and a WHSV of from 0.1 to 20, in particular from 1.0 to 10.0, g of starting material per g of catalyst per hour.

The reaction may be carried out either in a fixed bed or in a fluidized bed.

The reaction is generally effected under from 50 to 500, in particular from 150 to 350, bar.

The molar ratio of the starting materials amine/olefin is as a rule from 10:1 to 1:10, preferably from 3:1 to 1:2.

The process is preferably carried out continuously but may also be effected batchwise.

Sparingly volatile or solid starting materials can be used in dissolved form, for example in solution in tetrahydrofuran, toluene or petroleum ether. Furthermore, the starting material may be diluted with such solvents.

After the reaction, the products formed are isolated from the reaction mixture by a conventional method, for example by distillation or extraction, and, if necessary, are brought to the desired purity by further separation operations; unconverted starting materials may be recycled to the reactor. The byproducts obtained in the reaction, for example the acyclic monoadducts of the amines used, can advantageously either be put to another industrial use or be fed to a downstream complete cyclization.

The following catalysts are used for the Examples.

Catalyst A

A borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (weight ratio 50:50) at 170° C. under autogenous pressure in a stirred autoclave. The crystalline reaction product is filtered off, washed thoroughly, dried at 100° C. for 24 hours and then calcined at 500° C. for 24 hours. This borosilicate zeolite is composed of 94.2% by weight of $SiO_2$ and 2.3% by weight of $B_2O_3$. It is molded with boehmite in a weight ratio of 60:40 to give 2 mm extrudates, which are dried at 110° C. for 16 hours and calcined at 500° C. for 24 hours.

Catalyst B

Catalyst B is obtained by impregnating catalyst A with an aqueous $Cr(NO_3)_3$ solution and then drying the product at 130° C. for 2 hours and calcining it at 500° C. for 24 hours. The Cr content is 2.5% by weight.

Catalyst C

Catalyst C is prepared similarly to catalyst B, but is impregnated with an aqueous solution of Ce nitrate instead of Cr nitrate. The Ce content is 7.1% by weight.

EXAMPLES 1 to 3

10 ml of one of the catalysts described above are introduced into a 0.3 l stirred autoclave and the educts are added. If the educts are gaseous, they are forced in after the autoclave has been closed. The amount of starting material is such that the desired pressure is reached as autogenous pressure at the reaction temperature chosen. If this is not possible, the desired pressure is obtained using nitrogen.

EXAMPLES 4 and 5

The reaction is carried out under isothermal conditions in a tube reactor (coil, 0.6 cm internal diameter, 90 cm length) for not less than 6 hours. The reaction products are isolated and characterized by conventional methods. Quantitative determination of the reaction products and of the starting materials is carried out by gas chromatography.

The experimental results of Examples 1 to 5 are summarized in Table I.

TABLE I

| Example | Catalyst | Pressure [bar] | Temperature [°C.] | Ratio Diene/NH₃ | Conversion [%] | Selectivity TMP* [%] | Selectivity Open-chain intermediates [%] |
|---|---|---|---|---|---|---|---|
| 1 | A | 300 | 300 | 1:3 | 32 | 16.7 | 32.5 |
| 2 | B | 300 | 300 | 1:3 | 36 | 15.5 | 27.0 |
| 3 | C | 300 | 300 | 1:3 | 24 | 24.9 | 31.0 |
| 4 | A | 300 | 300 | 1:2.5 | 30.1 | 16.0 | 23.2 |
| 5 | B | 300 | 300 | 1:2.5 | 38.9 | 9.9 | 19.7 |

*TMP = 2,2,5,5-tetramethylpyrrolidine

The only selectivity-reducing byproducts of the reaction are isomerized octadienes. Dimerization products and other amines are not found.

We claim:

1. A process for the preparation of an N-heterocycle of the formula (I) or (II)

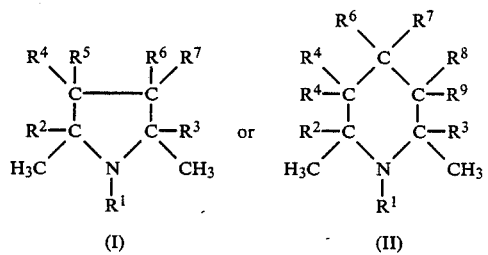

(I)    (II)

wherein $R^1$ and $R^4$ to $R^9$ are each hydrogen or alkyl, wherein each of $R^2$ and $R^3$ is alkyl, and wherein an olefin of the formula (III) or (IV)

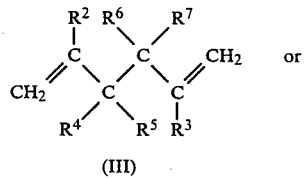

(III)

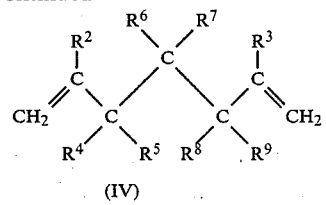

(IV)

where $R^2$ to $R^9$ have the above meanings, is reacted with NH₃ or with a primary amine of the formula H₂NR¹, where $R^1$ has the above meanings, in the presence of a zeolite as a catalyst.

2. The process as claimed in claim 1, wherein the olefin used is 2,5-dimethyl-1,5-hexadiene or 2,6-dimethyl-2,6-heptadiene.

3. The process as claimed in claim 1, wherein the catalyst used is a zeolite of the pentasil type.

4. The process as claimed in claim 3, wherein the catalyst used is an aluminosilicate zeolite of the pentasil type.

5. The process as claimed in claim 3, wherein the catalyst used is a borosilicate zeolite of the pentasil type.

6. The process as claimed in claim 3, wherein the catalyst used is an iron silicate zeolite of the pentasil type.

7. The process as claimed n claim 3, wherein the catalyst used is an aluminosilicate zeolite of the faujasite, erionite, chabasite or offretite type.

8. The process as claimed in claim 1, wherein the zeolite catalyst used has been doped with transition metals and/or noble metals and/or rare earth metals and/ or alkali metals and/or alkaline earth metals.

9. The process of claim 1, wherein $R^1$ is methyl, ethyl, cyclopentyl, cyclohexyl, phenyl or methyl-substituted phenyl; $R^4$ to $R^9$ is H or methyl and $R^2$ and $R^3$ are methyl.